(12) United States Patent
Hunneche et al.

(10) Patent No.: US 6,300,345 B1
(45) Date of Patent: Oct. 9, 2001

(54) CYANOGUANIDINES AS CELL PROLIFERATION INHIBITORS

(75) Inventors: Charlotte Schou Hunneche, Istanbul (TR); Hans Jørgen Petersen, Frederiksberg (DK)

(73) Assignee: Leo Pharmacuetical Products Ltd. A/S (Løvens kemiske Fabrik Produktionsaktieselskab), Ballerup (DK)

( * ) Notice: Subject to any disclaimer, the term of this patent is extended or adjusted under 35 U.S.C. 154(b) by 0 days.

(21) Appl. No.: 09/424,647

(22) PCT Filed: May 15, 1998

(86) PCT No.: PCT/DK98/00199

§ 371 Date: Nov. 26, 1999

§ 102(e) Date: Nov. 26, 1999

(87) PCT Pub. No.: WO98/54146

PCT Pub. Date: Dec. 3, 1998

(30) Foreign Application Priority Data

May 29, 1997 (GB) .................................................. 9711127

(51) Int. Cl.⁷ ........................ A61K 31/44; C07D 401/12

(52) U.S. Cl. ............................................. 514/332; 546/264
(58) Field of Search ............................... 514/332; 546/264

(56) References Cited

FOREIGN PATENT DOCUMENTS 94 06770    3/1994    (WO) .

OTHER PUBLICATIONS

Schou et al. Bioorganic and Medicinal Chemistry Letter, vol. 7, No. 24, p. 3095–3100.*

* cited by examiner

*Primary Examiner*—Jane Fan
(74) *Attorney, Agent, or Firm*—Pillsbury Winthrop LLP

(57) ABSTRACT

Compounds of the following formula are used for inhibiting cell proliferation:

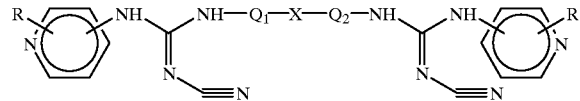

wherein R, Q1, Q2, X are as defined in the specification.

7 Claims, No Drawings

CYANOGUANIDINES AS CELL PROLIFERATION INHIBITORS

This application is the national phase of international application PCT/DK98/00199 filed May 15, 1998 now WO98/54,146 which designated the U.S.

This invention relates to a hitherto unknown class of compounds which shows strong activity in inhibiting undesirable cell proliferation of e.g. skin cells and cancer cells, to pharmaceutical preparations containing these compounds, to dosage units of such preparations, and to their use in the treatment and prophylaxis of diseases characterized by abnormal cell differentiation and/or cell proliferation such as e.g. psoriasis and cancer.

The compounds of the present invention are represented by the general formula I

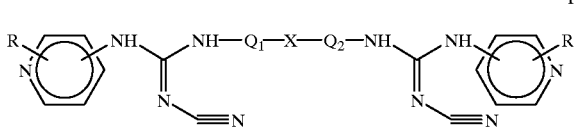

or their tautomeric forms, the attachment to the pyridine ring being in the 3- or 4-position, in which formula R stands for one or more substituents which can be the same or different and are selected from the group consisting of: hydrogen, halogen, trifluoromethyl, $C_1$–$C_4$ alkyl, alkoxy or alkyloxycarbonyl, nitro, amino or cyano and X stands for direct bonding, substituted $C_3$–$C_7$ cydoalkylene, divalent heterocyclic ring (with one or more nitrogen, oxygen or sulfur), arylene, oxygen, one or two sulfur or amino which can be substituted by hydrogen or $C_1$–$C_4$ alkyl; and $Q_1$ and $Q_2$ stands for $C_1$–$C_{10}$ divalent hydrocarbon radical which can be straight, branched, cyclic, saturated or unsaturated.

If the present compounds contain one or more asymmetric carbon atoms, these compounds may form optical isomers or diastereoisomers. The present invention also comprises such isomers, and mixtures of same.

The present salts of the compounds of formula I may be formed with pharmaceutically acceptable inorganic or organic acids, such as hydrochloric, hydrobromic and hydroiodic acid, phosphoric acid, sulfuric acid, nitric acid, 4-toluenesulfonic acid, methanesulfonic acid, formic acid, acetic acid, propionic acid, citric acid, tartaric acid, succinic acid, benzoic acid and maleic acid and lithium, sodium, potassium, magnesium, calcium salts, as well as with ammonia, C1–C6-alikylamines, C1–C6 alkanolamines, procaine, cycloalkylamines, benzylamines and heterocyclic amines.

Even if the present compounds are well absorbed after enteral administration, in some cases it can be advantageous to prepare suitable bioreversible derivatives of compounds of the invention, i.e. to prepare so-called prodrugs, preferably derivatives, the physicochemical properties of which leads to improved solubility at physiological pH and/or absorption and/or bioavailability of the compound in question.

Such derivatives are for instance pyridyl N-oxide derivatives of compounds of the invention, such compounds being prepared by oxidation of the pyridyl N by a suitable oxidizing agent, e.g. with 3-chloro-perbenzoic acid in an inert solvent, e.g. dichloromethane.

Other suitable methods to improve the physicochemical properties and/or solubility of the compounds concerned can be used as well.

N-Alkyl-N'-cyano-N"-pyridylguanidines, described in United Kingdom Patent No. 1,489,879, are potent potassium channel activators with a pronounced effect as pre-capillary vasodilators, reducing the total peripheral resistance in animals and in man, and are thus useful as antihypertensives. As stated in the International Patent No. PCT/DK93/00291, filing date Sep. 13, 1993, Publication No. WO 94/06770 the introduction of aryloxy-containing radicals into the aliphatic groups from the above-cited U.K. Patent has led to structures showing more specific pharmacological effects on isolated tissues and cells and with no or a negligible effect on $^{86}$Rb-efflux from potassium channels, as compared with the established effect of compounds covered by the above-mentioned U.K. Patent.

The compounds of the present invention inhibit the proliferation of various tumour cell lines in cultures at lower concentrations than the known compounds, confer Table 1 below, thus making them potentially useful in anfineoplastic chemotherapy.

The inhibition of tumour cell proliferation was studied using different types of human cancer cell lines. The cell lines under investigation were small cell lung carcinoma (NYH), non small cell lung carcinoma (NCI-H460), and breast cancer (MCF-7) using the following general procedure:

The cells were cultured in vitro for 24 hours in the presence of the compound under investigation. DNA synthesis was measured by incorporation of [3H]thymidine, and the median inhibitory concentrations ($IC_{50}$) of the compounds were calculated.

TABLE 1

Inhibition of tumour cell proliferation in vitro in human breast cancer (MCF-7), human small cell lung carcinoma (NYH) and human non small cell lung cancer (NCI-H460) cell lines by compounds of the following examples of the present invention.

| Compound from | MCF-7 $IC_{50}$ (nM) | NYH $IC_{50}$ (nM) | NCI-H460 $IC_{50}$ (nM) |
|---|---|---|---|
| Example No. 6 | 26 | 4.4 | 65 |
| Example No. 8 | 6.6 | 0.91 | 65 |
| Example No. 14 | 13 | 0.5 | 69 |
| Prior art A | 920 | 380 | >1000 |
| Prior art B | 250 | 45 | 67 |

A: N-Cyano-N'-(4-phenoxybutyl)-N"-4-pyridylguanidine, in PCT/DK93/00291, example 14.
B: N-Cyano-N'-(5-phenoxypentyl)-N"-4-pyridylguanidine, in PCT/DK93/00291, example 18.

The results show that the compounds of the present invention are able to inhibit the proliferation of tumour cells in vitro at the same or lower concentrations than the compounds A and B from PCT/DK93/00291.

The compounds of the invention are well tolerated and non-toxic and are exerting the described beneficial activities with no or minimal effect on the systemic blood pressure. In general, they may be administered by oral, intravenous, intraperitoneal, intranasal or transdermal routes.

The present invention also relates to methods for preparing the desired compounds of the general formula I. The compounds of the formula I may conveniently be prepared by standard procedures detailed in the art. The routes are outlined in the following reaction scheme.

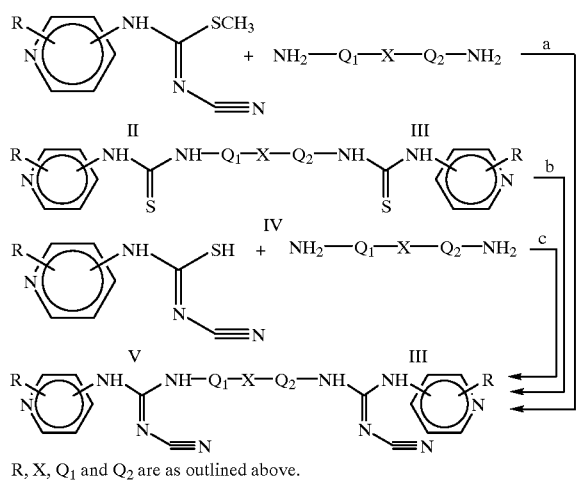

R, X, $Q_1$ and $Q_2$ are as outlined above.

a) DMAP, Et₃N, Pyridine, 95° C., 6h (General procedure 1).
b) DCCD, NH₂CN, Et₃N, DMF, 4 days. (General procedure 2).
c) Diisopropylethylamine, DCCD, DMF, 2 days. (General procedure 3).

The present compounds are intended for use in pharmaceutical compositions which are useful in the treatment of the above mentioned diseases.

The amount required of a compound of formula (I) (hereinafter referred to as the active ingredient) for therapeutic effect will, of course, vary both with the particular compound, the route of administration and the mammal under treatment. A suitable dose of a compound of formula (I) for systemic treatment is 0.1 to 400 mg per kilogram bodyweight, the most preferred dosage being 1.0 to 100 mg per kg of mammal bodyweight, for example 5 to 20 mg/kg; administered once or more times daily.

A daily dose (for adults) may amount to 1 mg to 10000 mg, preferably from 70–5000 mg, and in the veterinary practice correspondingly, in daily doses from 0.1 to 400 mg/kg bodyweight.

While it is possible for an active ingredient to be administered alone as the raw chemical, it is preferable to present it as a pharmaceutical formulation. Conveniently, the active ingredient comprises from 0.1% to 99% by weight of the formulation. Conveniently, dosage units of a formulation contain between 0.5 mg and 1 g of the active ingredient. For topical administration, the active ingredient preferably comprises from 1% to 20% by weight of the formulation but the active ingredient may comprise as much as 50% w/w. Formulations suitable for nasal or buccal administration may comprise 0.1% to 20% w/w. for example about 2% w/w of active ingredient.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and for human medical use, of the present invention comprise an active ingredient in association with a pharmaceutically acceptable carrier therefor and optionally other therapeutic ingredient(s). The carrier(s) must be "acceptable" in the sense of being compatible with the other ingredients of the formulations and not deleterious to the recipient thereof.

The formulations include those in a form suitable for oral, rectal, parenteral (including subcutaneous, intramuscular, intravenous and intraperitoneal) administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

In addition to the aforementioned ingredients, the formulations of this invention may include one or more additional ingredients, such as diluents, buffers, flavouring agents, binders, surface active agents, thickeners, lubricants, preservatives, e.g. methylhydroxybenzoate (including antioxidants), emulsifying agents and the like.

The compositions may further contain other therapeutically active compounds usually applied in the treatment of the above mentioned pathological conditions, e.g. antineoplastic agents which may result in synergistic effects on tumour cells.

The invention will now be further described in the following general procedures and examples:

The exemplified compounds I are listed in table 2.

TABLE 2

| Compound No. | Example No. | R | 3- or 4- Pyridyl | $Q_1$ | $Q_2$ | X |
|---|---|---|---|---|---|---|
| 101 | 1 | H | 4 | 1-$CH_2$ | 4-$CH_2$ | phenylene |
| 102 | 2 | H | 4 | $(CH_2)_5$ | $(CH_2)_4$ | — |
| 103 | 3 | H | 3 | $(CH_2)_3$ | $(CH_2)_4$ | — |
| 104 | 4 | H | 3 | $(CH_2)_2$ | $(CH_2)_2$ | S-S |
| 105 | 5 | H | 3 | $(CH_2)_3$ | $(CH_2)_3$ | — |
| 106 | 6 | H | 3 | $(CH_2)_6$ | $(CH_2)_6$ | — |
| 107 | 7 | H | 3 | $(CH_2)_4$ | $(CH_2)_4$ | — |
| 108 | 8 | H | 4 | $(CH_2)_5$ | $(CH_2)_5$ | — |
| 109 | 9 | H | 4 | $(CH_2)_4$ | $(CH_2)_4$ | — |
| 110 | 10 | H | 4 | 1-$CH_2$ | 4-$CH_2$ | cyclohexylene |
| 111 | 11 | H | 4 | $(CH_2)_3$ | $(CH_2)_3$ | — |
| 112 | 12 | H | 3 | $(CH_2)_2$ | $CH_2$ | — |
| 113 | 13 | H | 3 | $CH_2$ | $CH_2$ | — |
| 114 | 14 | H | 4 | $(CH_2)_6$ | $(CH_2)_6$ | — |
| 115 | 15 | H | 3 | $(CH_2)_5$ | $(CH_2)_5$ | — |
| 116 | 16 | 2,6-$Cl_2$ | 4 | $(CH_2)_5$ | $(CH_2)_5$ | — |
| 117 | 17 | 6-$OCH_3$ | 3 | $(CH_2)_5$ | $(CH_2)_5$ | — |

All melting points are uncorrected. For ¹H nuclear magnetic resonance (NMR) spectra (300 MHz) chemical shift values (δ) are quoted, unless otherwise specified, for hexadeuterodimethylsulfoxide solutions relative to internal tetramethylsilane (δ 0.00). The value for a multiplet (m), either defined (doublet (d), triplet (t), quartet (q)) or not at the approximate mid point is given unless a range is quoted (s singlet, b broad). The following abbreviations and formulas are used: DCCD (N,N'-dicyclohexylcarbodiimide), $NH_2CN$ (cyanamide), $Et_3N$ (triethylamine), DMF (dimethylformamide), DMAP (dimethylaminopyridine), MeOH (methanol), $CH_2Cl_2$ (methylenechloride) and DMSO-$d_6$ (hexadeuterodimethylsulfoxide).

General Procedure 1: Coupling of Compounds of the General Formula II with Compounds of the General Formula III Resulting in Compounds of the General Formula I.

A compound of the general formula II (6 mmol), a compound of the general formula III (3 mmol) and triethylamine (6 mmol) in pyridine (4 ml) were stirred at room temperature. 4-Dimethylaminopyridine (DMAP, 10 mg) was added and the solution was stirred at 95° C. for 6 hours.

To the mixture was added ether (10 ml) and the resulting suspension was filtered and washed with ether to leave the crystalline product of formula I.

General Procedure 2: Conversion of Compounds of the General Formula IV into Compounds of the General Formula I.

To a compound of the general formula IV (4 mmol) in dimethylformamide (3 ml) was added dicyclohexylcarbodiimide (12 mmol), cyanamide (12 mmol) and triethylamine (0.4 ml). The reaction mixture was kept at room temperature for 4 days, when it was evaporated in vacuo (0.5 mmHg).

The residue was triturated with 3 portions of petroleum ether. After decanting, the solid was stirred with acetone (15 ml), and the suspension was filtered and washed with acetone to leave a mixture of the product of general formula I and N,N'-dicyclohexylthiourea. Extraction with dilute hydrochloric acid (1 N, 16 ml) and reprecipitation from the filtrate with dilute sodium hydroxide afforded the crude product of the general formula I which was crystallized from ethanol.

General Procedure 3: Coupling of Compounds of the General Formula V with Compounds of the General Formula III Resulting in Compounds of the General Formula I.

A mixture of a compound of the general formula V (15 mmol), a compound of the general formula III (7.5 mmol) and diisopropylethylamine (15 mmol) in dimethylformamide (10 ml) was stirred at room temperature. To the resulting solution was added dicyclohexylcarbodiimide (16.5 mmol). The formed suspension was stirred for 2 days at room temperature and was then evaporated in vacuo (0.5 mmHg). The residue was triturated with 3 portions of petroleum ether (40 ml). After decanting, the solid was stirred with water (100 ml) containing hydrochloric acid (4 N, 6 ml). After filtration, the pH of the aqueous filtrate was adjusted to 7.5 with 2 N. sodium hydroxide. The precipitate was stirred at 0° C. and collected by filtration and washings with water. Recrystallization from aqueous acetone afforded the pure compound of the general formula I.

EXAMPLE 1

α,α'-Bis(N'-cyano-N''-4-pyridylguanidino)4-xylene (Compound 101)

General procedure 1.

Starting compound II: S-Methyl N-cyano-N'-4-pyridylisothiourea.

Starting compound III: 4-Xylenediamine.

Purification: Acetone was added to the reaction mixture. Filtration and washing with acetone resulted in the pure crystalline product.

$^1$H NMR (DMSO-$d_6$) δ: 9.38 (bs, 2H), 8.37 (d, 4H), 8.37 (bs, 2H), 7.32 (s, 4H), 7.19 (d, 4H), 4.47 (bs, 4H).

EXAMPLE 2

1.9-Bis(N'-cyano-N''-4-pyridylguanidino)nonane (Compound 102)

General procedure 1.

Starting compound II: S-Methyl N-cyano-N'-4-pyridylisothiourea.

Starting compound III: 1,9-Diaminononane.

Purification: Recrystallization from aqueous acetone.

$^1$H NMR (DMSO-$d_6$) δ: 9.35 (bs, 2H), 8.38 (m, 4H), 7.82 (bs, 2H), 7.20 (bd, 4H), 3.26 (bt, 4H), 1.52 (m, 4H), 1.28 (bs, 10H).

EXAMPLE 3

1,7-Bis(N'-cyano-N''-3-pyridylguanidino)heptane (Compound 103)

General procedure 1.

Starting compound II: S-Methyl N-cyano-N'-3-pyridylisothiourea.

Starting compound III: 1,7-Diaminoheptane.

Purification: The product was suspended in acetone, filtered and washed with acetone.

$^1$H NMR (DMSO-$d_6$) δ: 9.06 (bs, 2H), 8.45 (d, 2H), 8.33 (dd, 2H), 7.66 (m, 2H), 7.43 (bt, 2H), 7.37 (dd, 2H), 3.21 (q, 4H), 1.51 (m, 4H), 1.29 (bs, 6H).

EXAMPLE 4

2,2'-Bis(N'-cyano-N''-3-pyridylguanidino)diethyl disulfide (Compound 104)

General procedure 1.4 Equivalents of triethylamine were used.

Starting compound II: S-Methyl N-cyano-N'-3pyridylisothiourea.

Starting compound III: Bis (2-aminoethyl)disulfide, dihydrochloride.

Purification: Recrystallization from aqueous acetone.

$^1$H NMR (DMSO-$d_6$) δ: 9.25 (bs, 2H), 8.48 (d, 2H), 8.36 (dd, 2H), 7.67 (m, 2H) 7.54 (bt, 2H), 7.39 (dd, 2H), 3.52 (q, 4H), 2.92 (t, 4H).

EXAMPLE 5

1,6-Bis(N'-cyano-N''-3-pyridylguanidino)hexane (Compound 105)

General procedure 1.

Starting compound II: S-Methyl N-cyano-N'-3-pyridylisothiourea.

Starting compound III: 1,6-Diaminohexane.

Purification: The crystalline product was suspended in acetone, filtered and washed with acetone.

$^1$H NMR (DMSO-dr) δ: 8.98 (bs, 2H), 8.46 (d, 2H), 8.33 (dd, 2H), 7.66 (m, 2H), 7.44 (bs, 2H), 7.37 (dd, 2H), 3.22 (m, 4H), 1.52 (m, 4H), 1.30 (m, 4H).

EXAMPLE 6

1,12-Bis(N'-cyano-N''-3-pyridylguanidino)dodecane (Compound 106)

General procedure 1.

Starting compound II: S-Methyl N-cyano-N'-3-pyridylisothiourea.

Starting compound III: 1,12-Diaminododecane.
Purification: Recrystallization from aqueous acetone.
$^1$H NMR (DMSO-$d_6$) δ: 9.06 (bs, 2H), 8.45 (d, 2H), 8.33 (m, 2H), 7.66 (m, 2H), 7.43 (bs, 2H), 7.37 (dd, 2H), 3.21 (bs, 4H), 1.50 (m, 4H), 1.26 (bs, 16H).

EXAMPLE 7

1,8-Bis(N'-cyano-N"-3-pyridylguanidino)octane (Compound 107)

General procedure 1.

Starting compound II: S-Methyl N-cyano-N'-3pyridylisothiourea.
Starting compound III: 1,8-Diaminooctane.
Purification: Recrystallization from aqueous acetone.
$^1$H NMR (DMSO-$d_6$) δ: 9.06 (bs, 2H), 8.45 (d, 2H), 8.33 (dd, 2H), 7.66 (m, 2H), 7.41 (bt, 2H), 7.36 (dd, 2H), 3.21 (q, 4H), 1.51 (m, 4H), 1.29 (bs, 8H).

EXAMPLE 8

1,10-Bis(N'-cyano-N"-4-pyridylguanidino)decane (Compound 108)

General procedure 1.

Starting compound II: S-Methyl N-cyano-N'-4-pyridylisothiourea.
Starting compound III: 1,10-Diaminodecane.
Purification: Recrystallization from aqueous acetone.
$^1$H NMR (DMSO-$d_6$) δ: ~10 (bs, 2H), 8.42 (d, 4H), 8.02 (bt, 2H), 7.29 (bd, 4H), 3.29 (q, 4H), 1.52 (m, 4H), 1.27 (bs, 12H).

EXAMPLE 9

1,8-Bis(N'-cyano-N"-4-pyridylguanidino)octane (Compound 109)

General procedure 1.

Starting compound II: S-Methyl N-cyano-N'-4-pyridylisothiourea.
Starting compound III: 1,8-Diaminooctane.
Purification: Recrystallization from aqueous methanol.
$^1$H NMR (DMSO-$d_6$) δ: 9.34 (bs, 2H), 8.38 (m, 4H), 7.82 (bs, 2H), 7.20 (bd, 4H), 3.26 (t, 4H), 1.52 (m, 4H), 1.29 (bs, 8H).

EXAMPLE 10

1,4-Bis(N'-cyano-N"-4-pyrdylguanidinomethyl) cyclohexane (Compound 110)

General procedure 1.

Starting compound II: S-Methyl N-cyano-N'-4-pyridylisothiourea.
Starting compound III: 1,4-Bis(aminomethyl) cyclohexane.
Purification: The crystalline product was suspended in methanol, filtered and washed with methanol.
$^1$H NMR (DMSO-$d_6$) δ: 9.00 (bs, 2H), 8.38 (m, 4H), 7.81 (bs, 2H), 7.19 (m, 4H), 3.15 (d, 4H), 1.76 (m, 4H), 1.60-1.30 (m, 2H), 0.93 (m, 4H).

EXAMPLE 11

1,6-Bis(N'-cyano-N"-4-pyridylguanidino)hexane (Compound 111)

General procedure 2.

Starting compound IV: 1,6-Bis(N'-4-pyridylthioureido) hexane
Purification: Flash chromatography (Silica gel, eluent 0–22% MeOH in CH$_2$Cl$_2$) followed by crystallization from ether/acetone.
$^1$H NMR (DMSO-$d_6$) δ: 9.39 (bs, 2H), 8.38 (bd, 4H), 7.84 (bs, 2H), 7.21 (m, 4H), 3.27 (m, 4H), 1.53 (m, 4H), 1.32 (m, 4H).

EXAMPLE 12

1,3-Bis(N'-cyano-N"-3-pyridylguanidino)propane (Compound 112)

General procedure 3.

Starting compound V: N-Cyano-N'-3-pyridylthiourea.
Starting compound III: 1,3-Diaminopropane.
Purification: General procedure.
M.p. 148–148.5° C.
$^1$H NMR (DMSO-$d_6$) δ: 9.14 (bs, 2H), 8.55 (d, 2H), 8.42 (dd, 2H), 7.80 (m, 2H), 7.60–7.30 (m, 4H), 3.46 (t, 4H), 1.78 (m, 2H).

EXAMPLE 13

1,2-Bis(N'-cyano-N"-3-pyridylguanidino)ethane (Compound 113)

General procedure 3.

Starting compound V: N-Cyano-N'-3-pyridylthiourea.
Starting compound III: 1,2-Diaminoethane.
Purification: General procedure.
M.p. 146.5–147.5° C.
$^1$H NMR (DMSO-$d_6$) δ: 9.16 (bs, 2H), 8.48 (d, 2H), 8.38 (dd, 2H), 7.69 (bd, 2H), 7.43 (bs, 2H), 7.41 (dd, 2H), 3.38 (bs, 4H).

EXAMPLE 14

1,12-Bis(N'-cyano-N"-4-pyridylguanidino)dodecane (Compound 114)

General procedure 1

Starting compound II: S-Methyl N-cyano-N'-4-pyridylisothiourea.
Starting compound III: 1,12-Diaminododecane.
Purification: Flash chromatography (Silica gel, eluent 0–20% MeOH in CH$_2$Cl$_2$) followed by crystallisation from methanol/ether.
$^1$H NMR (DMSO-$d_6$) δ: 9.35 (bs, 2H), 8.38 (m, 4H), 7.83 (bt, 2H), 7.21 (bs, 4H), 3.26 (q, 4H), 1.51 (m, 4H), 1.25 (bs, 16H).

EXAMPLE 15

1,10-Bis(N'-cyano-N"-3-pyridylguanidino)decane (Compound 115)

General procedure 1

Starting compound II: S-Methyl N-cyano-N'-3pyridylisothiourea.
Starting compound III: 1,10-Diaminodecane.

Purification: Recrystallization from aqueous acetone.

$^1$H NMR (DMSO-d$_6$) δ: 9.06 (bs, 2H), 8.45 (d, 2H), 8.33 (dd, 2H), 7.66 (m, 2H), (bt, 2H), 7.37 (m, 2H), 3.21 (q, 4H), 1.50 (m, 4H), 1.27 (m, 12H).

EXAMPLE 16

1,10-Bis(N'-cyano-N"-(2,6-dichloro-4-pyridyl)guanidino)decane (Compound 116)

General procedure 1

Starting compound II: S-Methyl N-cyano-N'-(2,6-dichloro-4-pyridyl)isothiourea.

Starting compound III: 1,10-Diaminodecane.

Purification: Recrystallization from aqueous acetone and from acetone/ether.

1H NMR (DMSO-d6) δ: 9.82 (bs, 2H), 8.13 (bs, 2H), 7.31 (bs, 4H), 3.27 (m, 4H), 1.51 (m, 4H), 1.27 (m, 12H).

EXAMPLE 17

1,10-Bis(N'-cyano-N"-(2-methoxy-5-pyridyl)guanidino)decane (Compound 117)

General procedure 1

Starting compound II: S-Methyl N-cyano-N'-(2-methoxy-5-pyridyl) isothiourea.

Starting compound III: 1,10-Diaminodecane.

Purification: Flash chromatography (Eluent 1% NH$_3$(aq) and 0–30% MeOH in CH$_2$Cl$_2$).

1 H NMR (DMSO-d6) δ: 8.80 (bs, 2H), 8.00 (d, 2H), 7.55 (dd, 2H), 7.06 (bt, 2H), 6.82 (d, 2H), 3.84 (s, 6H), 3.14 (q, 4H), 1.46 (m, 4H), (m, 12H).

EXAMPLE 18

| Capsules |  |
|---|---|
| 1 Capsule contains: | |
| 1,10-Bis(N'-cyano-N"-4-pyridylguanidino)-decane (active compound) | 100 mg |
| Polyethylene Glycol | 962 mg |
| Gelatine Capsule no. 00 | |
| Gelatine | 122 mg |

EXAMPLE 19

| Tablets Manufacture of 10,000 tablets | | |
|---|---|---|
| I | 1,10-Bis(N'-cyano-N"-4-pyridylguanidino)-decane (active compound) | 10,000 kg |
|  | Cross carmellose sodium | 0,300 kg |
| II | Hydroxypropylmethyl cellulose, low viscosity type | 0,200 kg |
|  | Sorbimacrogol oleate | 0,010 kg |
|  | Purified water | q.s. |
| III | Crosscarmellose sodium | 0,200 kg |
|  | Coloidal anhydrous silica | 0,050 kg |
|  | Magnesium stearate | 0,050 kg |

I is mixed intimately in a highshear mixer, is wetted with II and granulated into a moist mass. The moist granulate is dried in a fluid-bed dryer at an inlet air temperature of 60° C. until the dried granulate has a water activity of 0.3–0.4 (=in equilibrium with air of 30–40% R.H.).

The dried granulate is passed through a sieve with mesh openings of 850 micro meters.

The sieved granulate is finally mixed with III in a cone mixer.

The finished granulate is compressed into tablets of mass 1071 mg and sufficient hardness.

What we claim is:

1. A compound of the formula I

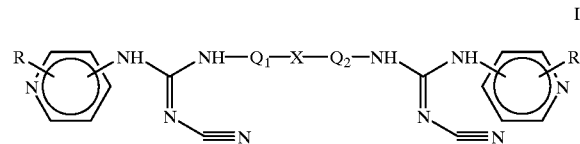

or their tautomeric forms, the attachment to the pyridine ring being in the 3- or 4-position, in which formula R stands for one or more substituents which can be the same or different and are selected from the group consisting of: hydrogen, halogen, trifluoromethyl, $C_1$–$C_4$ alkyl, alkoxy or alkyloxycarbonyl, nitro, amino or cyano and X stands for direct bonding, substituted $C_3$–$C_7$ cycloalkylene, arylene, oxygen, one or two sulfur or amino which can be substituted by hydrogen or $C_1$–$C_4$ alkyl; and $Q_1$ and $Q_2$ stands for $C_1$–$C_{10}$ divalent hydrocarbon radical which can be straight, branched, cyclic, saturated or unsaturated; and pharmaceutically acceptable, non-toxic salts and N-oxides thereof.

2. A compound according to formula I of claim 1, in which the attachment to the pyridine ring is in the 4-position, in which formula R stands for hydrogen and X stands for direct bonding, substituted $C_3$–$C_7$ cycloalkylene, arylene or one or two sulfur, and $Q_1$ and $Q_2$ stands for $C_1$–$C_{10}$ divalent hydrocarbon radical which can be straight, branched, saturated or unsaturated; and pharmaceutically acceptable, non-toxic salts and N-oxides thereof.

3. A salt according to claim 1 in which the salt is selected from the group consisting of salts formed with hydrochloric, hydrobromic and hydroiodic acid, phosphoric acid, sulphuric acid, nitric acid, p-toluenesulphonic acid, methanesulphonic acid, formic acid, acetic acid, propionic acid, citric acid, tartaric acid, and maleic acid, and lithium, sodium, potassium, magnesium, calcium salts, as well as salts with ammonia, $C_1$–$C_6$-alkylamines, $C_1$–$C_6$ alkanolamines, procaine, cycloalkylamines and benzylamines.

4. A compound of claim 1 which is selected from the group consisting of:

1,12-bis(N'-cyano-N"-3-pyridylguanidinododecane;

1,10-bis(N'-cyano-N"-4-pyridylguanidino)decane;

1,12-bis(N'-cyano-N"-4-pyridylguanidino)dodecane;

and their salts and pure enantiomeric forms.

5. A pharmaceutical composition containing a compound to claim 1 and a pharmaceutically acceptable carrier.

6. A method of inhibiting the proliferation of cancer cells selected from lung carcinoma and breast cancer cells in a host which comprises administering to said host an effective amount of one or more compounds according to claim 1.

7. Method for producing a compound of formula I according to claim 1, in which a) a compound of the general formula II

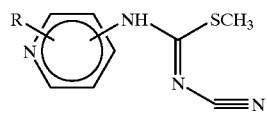

II in which R is as defined above, is reacted with a compound of the general formula III

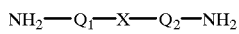

III in which $Q_1$, $Q_2$ and X are as defined above, in the presence of triethylamine or another tertiary amine and 4-dimethylaminopyridine in pyridine or an inert solvent at room temperature or above; or b) a compound of the general formula II

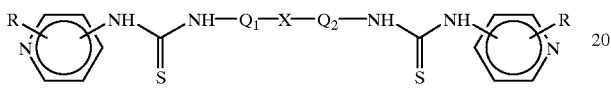

IV in which $Q_1$, $Q_2$, X and R are as defined above, is reacted with dicyclohexylcarbodiimide and cyanamide in the presence of triethytamine or another tertiary amine in acetonitrile or another inert solvent at room temperature or above; or c) a compound of the general formula V

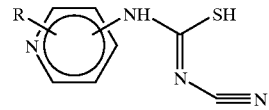

V in which R is as defined above, is reacted with a compound of the general formula III

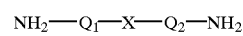

III in which $Q_1$, $Q_2$ and X are as defined above, in the presence of diisopropylethylamine or another tertiary amine in dimethytformamide or an inert solvent at roomtemperature or above.

* * * * *